(12) United States Patent
Hölzemann et al.

(10) Patent No.: US 7,262,216 B2
(45) Date of Patent: Aug. 28, 2007

(54) BENZOFURAN COMPOUNDS AND THEIR USE AS ANTIDEPRESSANTS AND ANXIOLYTICS

(75) Inventors: Günter Hölzemann, Seeheim-Jugenheim (DE); Henning Böttcher, Darmstadt (DE); Kai Schiemann, Seeheim-Jugenheim (DE); Timo Heinrich, Gross-Umstadt (DE); Joachim Leibrock, Pfungstadt (DE); Christoph Van Amsterdam, Darmstadt (DE); Gerd Bartoszyk, Weiterstadt (DE); Christoph Seyfried, Seeheim-Jugenheim (DE)

(73) Assignee: Merck Patent Gesellschaft, Darmstadt (DE)

( * ) Notice: Subject to any disclaimer, the term of this patent is extended or adjusted under 35 U.S.C. 154(b) by 21 days.

(21) Appl. No.: 10/545,170

(22) PCT Filed: Jan. 10, 2004

(86) PCT No.: PCT/EP2004/000125

§ 371 (c)(1),
(2), (4) Date: Aug. 11, 2005

(87) PCT Pub. No.: WO2004/072067

PCT Pub. Date: Aug. 26, 2004

(65) Prior Publication Data

US 2006/0142372 A1 Jun. 29, 2006

(30) Foreign Application Priority Data

Feb. 11, 2003 (DE) ................. 103 05 739

(51) Int. Cl.
*A61K 31/404* (2006.01)
*C07D 405/12* (2006.01)
(52) U.S. Cl. ...................... 514/414; 548/454
(58) Field of Classification Search ............ 546/277.4, 546/283.4; 548/426, 454; 549/382; 514/414
See application file for complete search history.

(56) References Cited

U.S. PATENT DOCUMENTS

| | | |
|---|---|---|
| 5,532,241 A | 7/1996 | Bottcher et al. |
| 5,723,614 A | 3/1998 | Bathe et al. |
| 6,333,339 B1 | 12/2001 | Boettcher et al. |
| 2004/0082594 A1 | 4/2004 | Bartoszyk |

FOREIGN PATENT DOCUMENTS

| | | |
|---|---|---|
| EP | 0648767 | 4/1995 |
| EP | 0738722 | 10/1996 |
| WO | WO9857953 | 12/1998 |
| WO | WO9903855 | 1/1999 |
| WO | WO 0072832 | 12/2000 |
| WO | WO 0240024 | 5/2002 |

OTHER PUBLICATIONS

Raymond et al, The recombinant 5-HT1A receptor: G protein coupling and signalling pathways, Aug. 1999, British Journal of Pharmacology, 127, p. 1751-1764.*

* cited by examiner

*Primary Examiner*—Kamal A. Saeed
*Assistant Examiner*—Karen Cheng
(74) *Attorney, Agent, or Firm*—Millen, White, Zelano & Branigan, P.C.

(57) ABSTRACT

Novel benzofuran derivatives of the formula (I) in which $R^1$, $R^2$, X, Y, Z and m have the meanings indicated in Patent Claim 1, they have a strong affinity to the 5-$HT_{1A}$ receptors. The compounds inhibit serotonin reuptake, exhibit serotonin-agonistic and -antagonistic properties and are suitable as antidepressants, anxiolytics, antipsychotics, neuroleptics and/or antihypertonics (I)

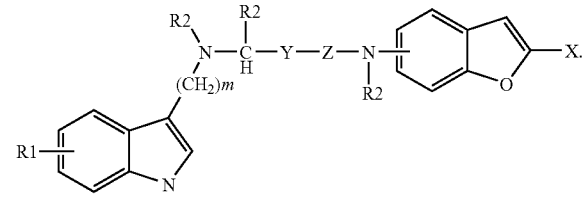

27 Claims, No Drawings

BENZOFURAN COMPOUNDS AND THEIR USE AS ANTIDEPRESSANTS AND ANXIOLYTICS

CROSS REFERENCE TO RELATED APPLICATIONS

This application is a U.S. National Phase application under 35 U.S.C. § 371 of PCT Application No. PCT/EP2004/000125, filed Jan. 10, 2004, which claims priority from German Application No. 103 05 739.0, filed on Feb. 11, 2003.

The invention relates to benzofuran derivatives of the formula I

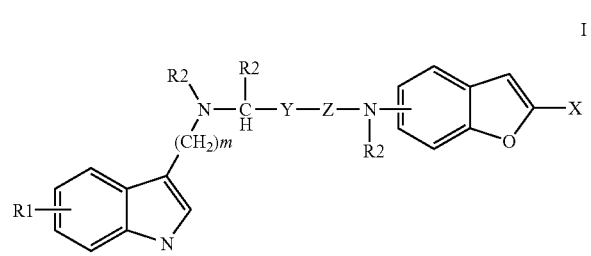

in which
$R^1$ denotes mono- or disubstitution by OH, OA, CN, Hal, COR or $CH_2R$
R denotes OH, OA, $NH_2$, NHA or $NA_2$
$R^2$ denotes H, A, Ar, $CH_2$—Ar or $CH_2$—OH
A denotes alkyl having 1, 2, 3, 4, 5 or 6 atoms
Z denotes $CH_2$ or CO
Y denotes a bond or $CH_2$
X denotes $CH_2OH$, $CH_2OA$ or COR
m denotes 2, 3, 4, 5 or 6, and pharmaceutically usable derivatives, solvates and stereoisomers thereof, including mixtures thereof in all ratios.

The invention was based on the object of finding novel compounds having valuable properties, in particular those which are used for the preparation of medicaments.

Other indole derivatives are known from EP 648767 (Merck), WO 00/78716 (Toray Industries, Inc.) or from WO 90/05721.

It has been found that the compounds of the formula I according to the invention and physiologically acceptable acid-addition salts thereof are well tolerated and have valuable pharmacological properties since they have actions on the central nervous system, in particular 5-HT reuptake-inhibiting actions, in that they influence serotoninergic transmission. In particular, they have a strong affinity to the $5\text{-HT}_{1A}$ receptors.

Since the compounds also inhibit serotonin reuptake, they are particularly suitable as antidepressants and anxiolytics. The compounds exhibit sero-tonin-agonistic and -antagonistic properties. They inhibit the binding of tritiated serotonin ligands to hippocampal receptors (Cossery et al., European J. Pharmacol. 140 (1987), 143-155) and inhibit synaptosomal serotonin reuptake (Sherman et al., Life Sci. 23 (1978), 1863-1870). Ex-vivo demonstration of serotonin reuptake inhibition is carried out using synaptosomal uptake inhibition (Wong et al., Neuropsychopharmacol. 8 (1993), 23-33) and p-chloroamphetamine antagonism (Fuller et al., J. Pharmacol. Exp.Ther. 212 (1980), 115-119).

The binding properties of the compounds of the formula I can be determined by known $5\text{-HT}_{1A}$ (serotonin) binding tests ($5\text{-HT}_{1A}$ (serotonin) binding test: Matzen et al., J. Med. Chem., 43,1149-1157, (2000) in particular page 1156 with reference to Eur. J. Pharmacol.: 140, 143-155 (1987).

The compounds according to the invention can be employed for the treatment of diseases which are associated with the serotonin neurotransmitter system and in which high-affinity serotonin receptors ($5\text{-HT}_{1A}$ receptors) are involved.

The compounds of the formula I are therefore suitable both in veterinary and also in human medicine for the treatment of dysfunctions of the central nervous system and of inflammation. They can be used for the pro-phylaxis and combating of the consequences of cerebral infarction (apoplexy cerebri), such as strokes and cerebral ischaemia, and for the treatment of extrapyramidal motor side effects of neuroleptics and of Parkinson's disease, for the acute and symptomatic therapy of Alzheimer's disease and for the treatment of amyotrophic lateral sclerosis. They are likewise suitable as therapeutic agents for the treatment of brain and spinal cord trauma. In particular, however, they are suitable as medicament active ingredients for anxiolytics, antidepressants, antipsychotics, neuroleptics, antihypertonics and/or for positively influencing obsessive-compulsive disorder (OCD), anxiety states, panic attacks, psychoses, anorexia, delusional obsessions, migraine, Alzheimer's disease, sleeping disorders, tardive dyskinesia, learning disorders, age-dependent memory impairment, eating disorders, such as bulimia, drugs misuse and/or sexual dysfunctions.

An important indication for the administration of the compound of the general formula I are psychoses of all types, in particular also mental illnesses from the schizophrenia group. In addition, the compounds can also be employed for reducing defects in cognitive ability, i.e. for improving learning ability and memory. The compounds of the general formula I are also suitable for combating the symptoms of Alzheimer's disease. In addition, the substances of the general formula I according to the invention are suitable for the prophylaxis and control of cerebral infarctions (apoplexy cerebri), such as cerebral strokes and cerebral ischaemia. The substances are furthermore suitable for the treatment of diseases such as pathological anxiety states, overexcitation, hyperactivity and attention disorders in children and youths, severe developmental disorders and disorders of social behaviour with mental retardation, depression, obsessive disorders in the narrower (OCD) and broader sense (OCSD) certain sexual dysfunctions, sleeping disorders and disorders in nutrient uptake, and psychiatric symptoms as part of age dementia and dementia of the Alzheimer's type, i.e. diseases of the central nervous system in the broadest sense.

The compounds of the formula I are likewise suitable for the treatment of extrapyramidal motor diseases, for the treatment of side effects which occur in the treatment of extrapyramidal motor diseases with conventional anti-Parkinson's medicaments, or for the treatment of extrapyramidal symptoms (EPS) induced by neuroleptics.

Extrapyramidal motor diseases are, for example, idiopathic Parkinson's disease, parkinsonian syndrome, dyskinetic choreatic or dystonic syndromes, tremor, Gilles de la Torette syndrome, ballismus, muscle cramps, restless legs syndrome, Wilson's disease, Lewy bodies dementia, Huntington's and Tourette's syndrome.

The compounds according to the invention are also particularly suitable for the treatment of neurodegenerative diseases, such as, for example, lathyrism, Alzheimer's, Parkinson's, and Huntington's.

The compounds of the formula I are particularly suitable for the treatment of side effects which occur in the treatment of idiopathic Parkinson's disease with conventional Parkinson's medicaments. They can therefore also be used as add-on therapy in the treatment of Parkinson's disease. Known Parkinson's medicaments are drugs such as L-dopa (levodopa) and L-dopa combined with benserazide or carbidopa, dopamine agonists, such as bromocriptine, apomorphine, cabergoline, pramipexole, ropinirole, pergolide, dihydro-α-ergocriptine or lisuride, and all medicaments which effect stimulation of the dopamine receptor, inhibitors of catechol O-methyl transferase (COMT), such as entacapone or tolcapone, inhibitors of monoamine oxidase (MAO), such as selegiline, and antagonists of N-methyl D-aspartate (NMDA) receptors, such as amantadine or budipine.

The compounds of the general formula I and tolerated salts and solvates thereof can thus be employed as active ingredients for medicaments, such as anxiolytics, antidepressants, neuroleptics and/or antihypertonics. A measure of the uptake of a medicament active ingredient in an organism is its bioavailability.

If the medicament active ingredient is supplied intravenously to the organism in the form of an injection solution, its absolute bioavailability, i.e. the fraction of the drug which reaches the systemic blood, i.e. the general circulation, in unchanged form, is 100%.

In the case of oral administration of a therapeutic active ingredient, the active ingredient is generally in the form of a solid in the formulation and must therefore first be dissolved so that it is able to overcome the entry barriers, for example the gastrointestinal tract, the oral mucous membrane, nasal membranes or the skin, in particular the stratum corneum, or can be absorbed by the body. Pharmacokinetic data, i.e. on the bioavailability, can be obtained analogously to the method of J. Shaffer et al, J. Pharm. Sciences, 1999, 88, 313-318.

A further measure of the absorbability of a therapeutic active ingredient is the logD value, since this value is a measure of the lipophilicity of a molecule.

If the compounds of the general formula I are optically active, the formula I covers both each isolated optical antipode and also the corresponding possibly racemic mixtures in any conceivable composition.

The term solvates of the compounds of the formula I is taken to mean adductions of inert solvent molecules onto the compounds of the formula I which form owing to their mutual attractive force. Solvates are, for example, mono- or dihydrates or addition compounds with alcohols, such as, for example, with methanol or ethanol.

The invention relates to the compounds of the formula I and salts and solvates thereof according to Claim 1 and to a process for the preparation of compounds of the formula I and salts, solvates and stereoisomers thereof, characterised in that a) a compound of the formula II

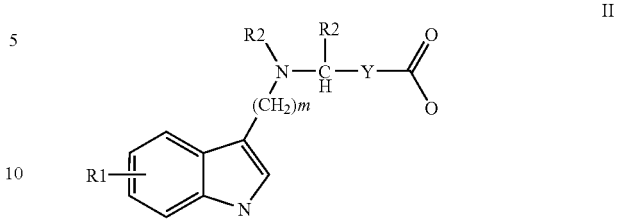

in which
$R^1$, $R^2$, Y and m have the meanings indicated in Claim 1 is reacted with a compound of the formula III

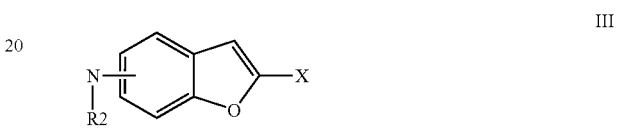

in which
$R^2$ and X have the meanings indicated in Claim 1, or
b) a compound of the formula IV

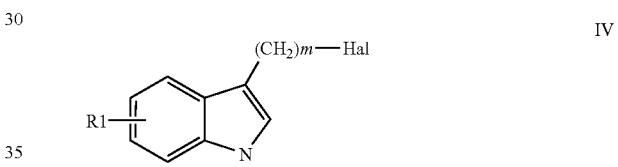

in which $R^1$, Hal and m have the meanings indicated in Claim 1, is reacted with a compound of the formula V

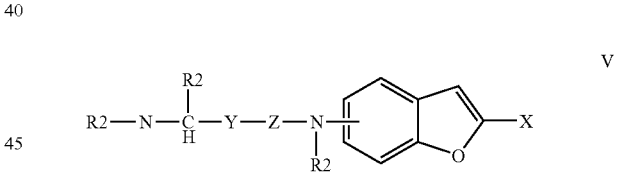

in which
$R^2$, X, Y and Z have the meanings indicated in Claim 1, and/or
a basic or acidic compound of the formula I is converted into one of its salts or solvates by treatment with an acid or base.

The term pharmaceutically usable derivatives is taken to mean, for example, the salts of the compounds according to the invention and so-called prodrug compounds.

The term prodrug derivatives is taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as described, for example, in Int. J. Pharm. 115, 61-67 (1995).

A denotes alkyl having 1, 2, 3, 4, 5 or 6 C atoms, preferably methyl, ethyl, propyl, isopropyl, butyl, isobutyl, secbutyl, tert-butyl, pentyl, hexyl, trifluoromethyl, pentafluoroethyl or 1,1,1-trifluoroethyl. Particular preference is given to methyl or ethyl.

A also denotes cycloalkyl.

Cycloalkyl preferably denotes cyclopropyl, cyclobutyl, cyclopentyl, cyclohexyl or cycloheptyl.

Ar preferably encompasses an unsubstituted or mono- or polysubstituted benzene ring, for example an unsubstituted or substituted phenyl radical or an unsubstituted or mono- or polysubstituted system of benzene rings, such as, for example, anthracene, phenanthrene or naphthalene ring systems. Examples of suitable substituents include alkyl, alkoxy, oxo, hydroxyl, mercapto, amino, nitro, cyano and halogen radicals.

Hal preferably denotes F, Cl, Br, but also I.

OA preferably denotes methoxy, ethoxy, propoxy, isopropoxy, butoxy or tert-butoxy.

R preferably denotes $NH_2$, O-methyl and O-ethyl.

$R^1$ preferably denotes CN or F.

R preferably denotes H or methyl.

Z preferably denotes $CH_2$ or CO.

X preferably denotes $COOC_2H_5$, $CONH_2$ or $CH_2OH$.

Y preferably denotes a bond or $CH_2$ m preferably denotes 2 or 4.

Accordingly, the invention relates, in particular, to the compounds of the formula I in which at least one of the said radicals has one of the preferred meanings indicated above.

The compounds of the formula I according to Claim 1 and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se, which are not mentioned here in greater detail.

If desired, the starting materials can also be formed in situ so that they are not isolated from the reaction mixture, but instead are immediately converted further into the compounds of the formula I according to Claim 1.

The starting compounds of the formula II and III are generally known. If they are novel, however, they can be prepared by methods known per se.

Compounds of the formula I can be prepared by reaction of the compounds of the formula II with compounds of the formula III under standard conditions.

The reaction is generally carried out in an inert solvent, in the presence of an acid-binding agent, preferably an alkali or alkaline earth metal hydroxide, carbonate or bicarbonate, or another salt of a weak acid of the alkali or alkaline earth metals, preferably of potassium, sodium, calcium or caesium. The addition of an organic base, such as ethyldiisopropylamine, triethylamine, dimethylaniline, pyridine or quinoline, may also be favourable. The reaction time, depending on the conditions used, is between a few minutes and 14 days, the reaction temperature is between about 0° and 150°, normally between 20° and 130°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, N-methylpyrrolidone, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Compounds of the formula I can furthermore be obtained by reacting compounds of the formula IV with compounds of the formula V. The starting compounds of the formula IV and V are generally known. If they are novel, however, they can be prepared by methods known per se. The reaction conditions are analogous to those of the reaction between compounds of the formula II and compounds of the formula III.

Esters can be saponified, for example, using acetic acid or using NaOH or KOH in water, water/THF or water/dioxane, at temperatures between 0 and 100°.

Free amino groups can furthermore be acylated in a conventional manner using an acid chloride or anhydride or alkylated using an unsubstituted or substituted alkyl halide or reacted with $CH_3$—C(=NH)—OEt, advantageously in an inert solvent, such as dichloromethane or THF, and/or in the presence of a base, such as triethylamine or pyridine, at temperatures between −60 and +30°.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexane-carboxylic acid, glucose 1-phosphate, naphthalenemono- and disulfonic acids or laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate).

The invention also relates to the compounds of the formula I according to Claim 1 and physiologically acceptable salts or solvates thereof as medicament active ingredients.

The invention furthermore relates to compounds of the formula I and physiologically acceptable salts or solvates thereof as $5HT_{1A}$ agonists and as inhibitors of 5-HT reuptake.

The invention also relates to the compounds of the formula I according to Claim 1 and physiologically acceptable salts or solvates thereof for use in combating diseases.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

The invention furthermore relates to the use of the compounds of the formula I and/or physiologically acceptable salts thereof for the preparation of a medicament (pharmaceutical composition), in particular by non-chemical methods. They can be converted here into a suitable dosage form together with at least one solid, liquid and/or semi-liquid excipient or adjuvant and, if desired, in combination with one or more further active ingredients.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

The invention furthermore relates to the use of a compound of the general formula I and/or pharmaceutically usable derivatives, solvates and stereoisomers thereof, including mixtures thereof in all ratios, for the preparation of a medicament which is suitable for the treatment of human or animal diseases, in particular diseases of the central nervous system, such as pathological stress states, depression and/or psychoses, for reducing side effects in the treatment of high blood pressure (for example with a-methyldopa), for the treatment of endocrinological and/or gynaecological diseases, for example for the treatment of agromegaly, hypogonadism, secondary amenorrhoea, postmenstrual syndrome and undesired lactation in puberty and for the prophylaxis and therapy of cerebral diseases (for example migraine), in particular in geriatrics, in a similar manner to certain ergot alkaloids, and for the control and prophylaxis of cerebral infarction (apoplexy cerebri), such as cerebral strokes and cerebral ischaemia, for the treatment of extrapyramidal motor diseases, for the treatment of side effects which occur in the treatment of extrapyramidal motor diseases with conventional anti-Parkinson's medicaments, or for the treatment of extrapyramidal symptoms (EPS) induced by neuroleptics. In addition, the pharmaceutical compositions and medicaments which comprise a compound of the general formula I are suitable for improving cognitive ability and for the treatment of the symptoms of Alzheimer's disease.

In particular, medicaments of this type are suitable for the treatment of mental illnesses from the schizophrenia group and for combating psychotic anxiety states. For the purposes of the invention, the term treatment includes prophylaxis and therapy of human or animal diseases.

The invention furthermore relates to the use of compounds of the formula I and/or pharmaceutically usable derivatives, solvates and stereoisomers thereof, including mixtures thereof in all ratios, for the preparation of a medicament for combating diseases which are associated with the serotonin neurotransmitter system and in which high-affinity serotonin receptors ($5\text{-}HT_{1A}$ receptors) are involved.

The invention furthermore relates to the use of compounds of the formula I and/or pharmaceutically usable derivatives, solvates and stereoisomers thereof, including mixtures thereof in all ratios, for the preparation of a medicament as anxiolytic, antidepressant, neuroleptic and/or antihypertensive.

The substances of the general formula I are normally administered analogously to known, commercially available pharmaceutical compositions (for example bromocriptine and dihydroergocornine), preferably in doses of between 0.2 and 500 mg, in particular of between 0.2 and 15 mg, per dosage unit. The daily dosage unit is between 0.001 and 10 mg per kg of body weight. Low doses (of between 0.2 and 1 mg per dosage unit, 0.001 to 0.005 mg per kg of body weight) are particularly suitable for pharmaceutical compositions for the treatment of migraine. A dose of between 10 and 50 mg per dosage unit is preferred for other indications. However, the dose to be administered depends on a multiplicity of factors, for example on the efficacy of the corresponding component, the age, the body weight and the general state of health of the patient.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may comprise, for example, separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel, by preparative HPLC and/or by crystallisation. The purified compounds are optionally freeze-dried.

Mass spectrometry (MS): EI (electron impact ionisation) $M^+$
FAB (fast atom bombardment) $(M + H)^+$
ESI (electrospray ionisation) $(M + H)^+$ (unless stated otherwise)

EXAMPLE 1

Preparation of 3-[4-(5-cyano-1H-indol-3-yl)butylamino]-N-(2-hydroxy-methylbenzofuran-5-yl)propionamide

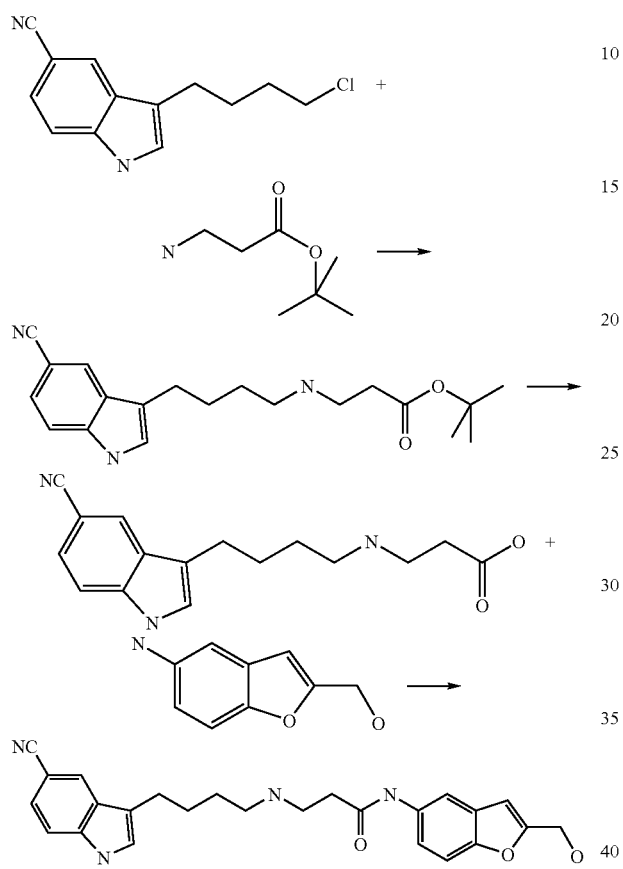

320 mg of 3-[4-(5-cyano-1H-indol-3-yl)butylamino]propionic acid and 147 mg of (5-aminobenzofuran-2-yl)methanol are dissolved in 30 ml of DMF. 290 mg of TBTU (o-benzotriazol-1-yl-n,n,n',n'-tetramethyluronium tetrafluoroborate) and 41 mg of HOBt (1-hydroxybenzotriazole) are added. The solution is neutralised using 0.3 ml of triethylamine. The batch is stirred overnight at room temperature.

The reaction mixture is evaporated, the residue is taken up in ethyl acetate and washed 3× with semi-concentrated NaHCO$_3$ solution. The org. phase is dried over Na$_2$SO$_4$ and evaporated in a rotary evaporator. For purification, a preparative HPLC is carried out.

Yield: 17 mg of white solid substance, TFA salt
[M+H]$^+$431 (HPLC-MS)
Rf=0.7 (CH$_2$Cl$_2$: MeOH (8:2)

3-[4-(5-Cyano-1H-indol-3-yl)butylamino]propionic acid 470 mg of tert-butyl 3-[4-(5-cyano-1H-indol-3-yl)butylamino]propionate are dissolved in 10 ml of HCl/dioxane (4N) and stirred for five hours. The solution is evaporated in a rotary evaporator, giving the HCl salt of the desired compound.
Rf=0.1 (CH$_2$Cl$_2$: MeOH (8:2)

tert-Butyl 3-[4-(5-cyano-1H-indol-3-yl)butylamino]propionate 1.5 g of 3-(4-chlorobutyl)-1H-indole-5-carbonitrile and 1.1 g of β-alanine tert-butyl ester are dissolved in 30 ml of acetonitrile, and 2.1 ml of triethylamine are added. The mixture is boiled under reflux for 3 days.

After cooling, the reaction solution is evaporated in a rotary evaporator, the residue is taken up in water. The alkaline solution is extracted with ethyl acetate. The org. phase is dried and evaporated in a rotary evaporator, giving an oil, which is purified by silica gel chromatography.

Yield: 470 mg of desired product
[M+H]$^+$342 (HPLC-MS)
Rf=0.6 (CH$_2$Cl$_2$: MeOH (8:2)

(5-Aminobenzofuran-2-yl)methanol 2 g of ethyl 5-aminobenzofuran-2-carboxylate are suspended in 129 ml of THF. 660 mg of lithium aluminium hydride are initially introduced in 120 ml of THF and slowly added dropwise the suspension of the ester. The mixture is boiled under reflux for 3 hours.

The reaction solution is cooled, and 160 ml of water are added dropwise with ice-cooling and under nitrogen, and the mixture is stirred for a further 15 min. 200 ml of ethyl acetate are then added to the entire mixture, which is extracted with a total of 600 ml (3×200 ml) of ethyl acetate. The org. phase is dried, filtered and evaporated.

Yield: 1.5 g of the desired substance
Rf=0.5 (CH$_2$C12: MeOH (9:1)

EXAMPLE 2

Preparation of 3-(4-{[2-(2-hydroxymethylbenzofuran-5-ylamino)ethyl]-methylamino}butyl)-1H-indole-5-carbonitrile

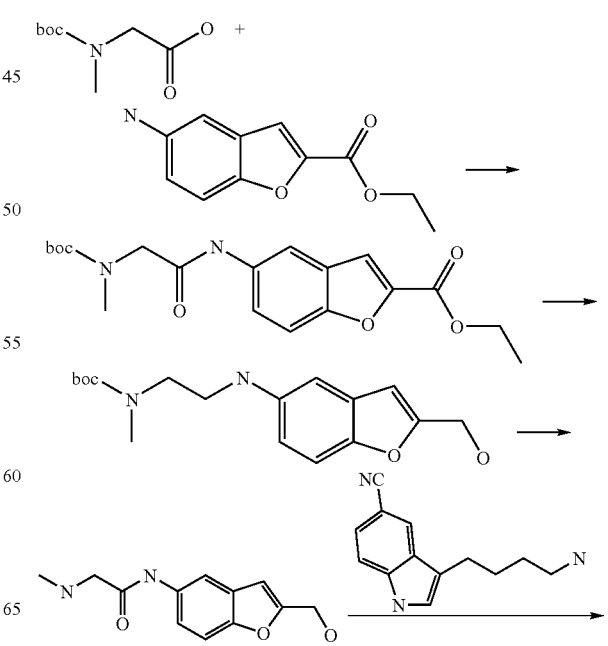

-continued

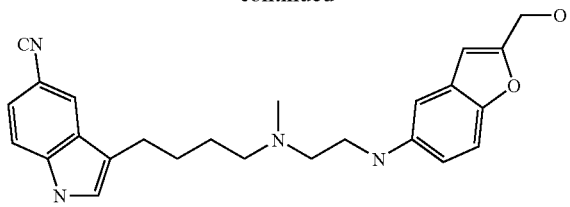

54 mg of 3-(4-chlorobutyl)-1H-indole-5-carbonitrile and 59 mg of [5-(2-methylaminoethylamino)benzofuran-2-yl]methanol are dissolved in 30 ml of acetonitrile, and 0.07 ml of triethylamine is added. The mixture is boiled under reflux for about 3 days.

After cooling, the reaction solution is evaporated in a rotary evaporator, and the residue is taken up in water. The alkaline solution is extracted with ethyl acetate. The org. phase is dried and evaporated in a rotary evaporator.

For purification, a preparative HPLC is carried out.

Yield: 5.9 mg of white substance, TFA salt $[M+H]^+$ 417 (EI-MS)

[5-(2-Methylaminoethylamino)benzofuran-2-yl]methanol 74 mg of tert-butyl [2-(2-hydroxymethylbenzofuran-5-ylamino)ethyl]methylcarbamate are dissolved in 10 ml of HCl/dioxane (4N) and stirred at room temperature for two hours. Evaporation in a rotary evaporator gives 59 mg of the desired product (HCl salt).

tert-Butyl [2-(2-hydroxymethylbenzofuran-5-ylamino)ethyl]methylcarbamate 380 mg of lithium aluminium hydride are suspended in 40 ml of THF, and 750 mg of ethyl 5-[2-(tert-butoxycarbonylmethylamino)acetylamino]benzofuran-2-carboxylate in 30 ml of THF are slowly added dropwise under nitrogen. The mixture is boiled under reflux for 30 hours.

The reaction mixture is cooled, and 50 ml of $H_2O$ is carefully added with ice-cooling and under $N_2$. Dichloromethane is then added, undissolved constituents are filtered off with suction and extracted 2× with $CH_2Cl_2$. The org. phase is dried and evaporated in a rotary evaporator. The crude product is purified by silica gel chromatography.

Yield: 77 mg of desired product.

$[M+H]^+$ 321 (HPLC-MS)

Ethyl 5-[2-(tert-butoxycarbonylmethylamino)acetylamino]benzofuran-2-carboxylate 50 ml of DMF are added to 0.95 g of Boc-sarcosine and 1.21 g of ethyl 5-aminobenzofuran-2-carboxylate. 1.77 g of TBTU and 0.23 g of HOBt are then added, and the mixture is neutralised using 4 ml of triethylamine. The mixture is stirred overnight at room temperature.

The DMF is distilled off, and the residue is mixed with about 50 ml of ethyl acetate, washed 3× with 30 ml of 5% citric acid, 1× with 50 ml of sat. NaCl soln., 3× with 30 ml of semi-saturated sodium hydrogencarbonate soln. and 1× with 50 ml of sat NaCl soln. The org. phase is dried using sodium sulfate, filtered and evaporated in a rotary evaporator. The oil remaining crystallises.

Yield: 1.49 g of red-brown substance

The following compounds are prepared by analogous procedures.

EXAMPLE 3

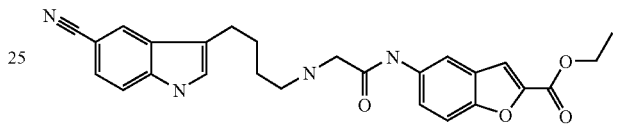

Ethyl 5-{2-[4-(5-cyano-1H-indol-3-yl)butylamino]ethanoylamino}benzofuran-2-carboxylate $[M+H]^+$ 459 (MALDI-MS)

EXAMPLE 4

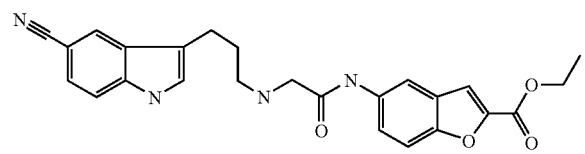

Ethyl 5-{2-[3-(5-cyano-1H-indol-3-yl)propylamino]ethanoylamino}benzofuran-2-carboxylate $[M+H]^+$ 445 (MALDI-MS)

EXAMPLE 5

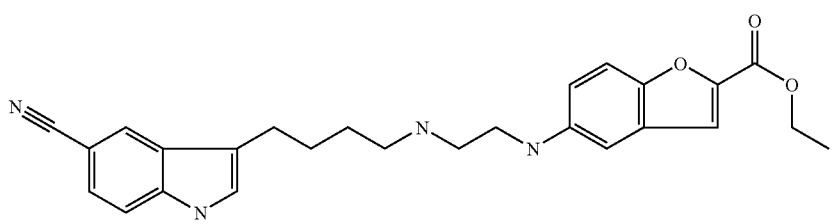

Ethyl 5-{2-[4-(5-cyano-1H-indol-3-yl)butylamino]ethylamino}benzofuran-2-carboxylate

[M+H]⁺445 (EI-MS)

EXAMPLE 6

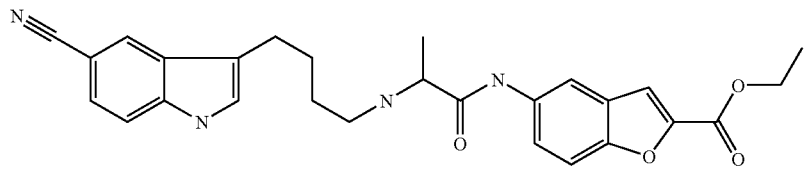

Ethyl 5-{2-[4-(5-cyano-1H-indol-3-yl)butylamino]propanoylamino}benzofuran-2-carboxylate

[M+H]⁺473 (EI-MS)

EXAMPLE 7

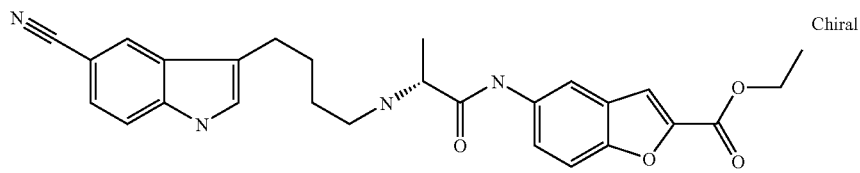

Ethyl (R)-5-{2-[4-(5-cyano-1H-indol-3-yl)butylamino]propanoylamino}-benzofuran-2-carboxylate

[M+H]⁺473 (MALDI-MS)

EXAMPLE 8

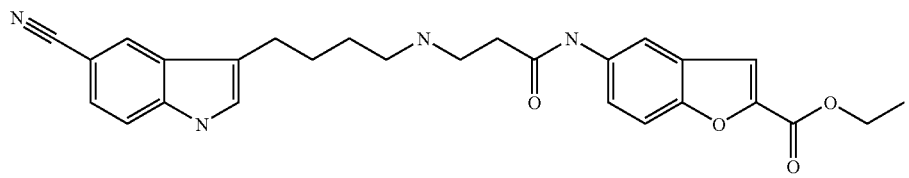

Ethyl 5-{3-[4-(5-cyano-1H-indol-3-yl)butylamino]propanoylamino}benzofuran-2-carboxylate

[M+H]⁺473 (MALDI-MS)

EXAMPLE 9

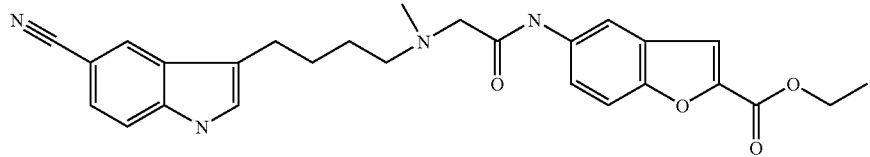

Ethyl 5-(2-{[4-(5-cyano-1H-indol-3-yl)butyl]methylamino}ethanoylamino)-benzofuran-2-carboxylate

[M+H]⁺473 (ESI-MS)

EXAMPLE 10

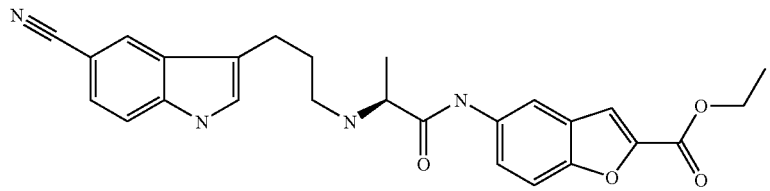

Ethyl (S)-5-{2-[3-(5-cyano-1H-indol-3-yl)propylamino]propanoylamino}-benzofuran-2-carboxylate

[M+H]⁺459 (MALDI-MS)

EXAMPLE 11

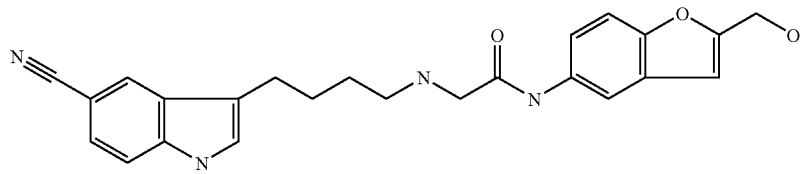

2-[4-(5-Cyano-1H-indol-3-yl)butylamino]-N-(2-hydroxymethylbenzofuran-5-yl)acetamides

[M+H]⁺417 (ESI-MS)

EXAMPLE 12

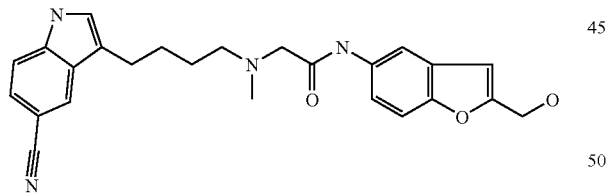

C{[4-(5-Cyano-1H-indol-3-yl)butyl]methylamino}-N-(2-hydroxymethyl-benzofuran-5-yl)acetamides

[M+H]⁺431 (EI-MS)

EXAMPLE 13

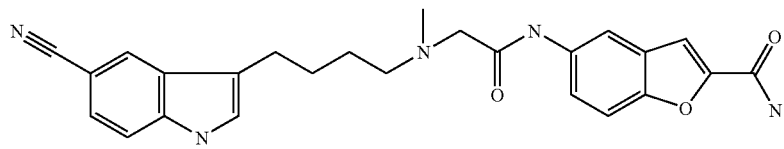

5-(2-{[4-(5-Cyano-1H-indol-3-yl)butyl]methylamino}ethanoylamino)benzofuran-2-carboxamides

[M+H]+444 (EI-MS)

EI-MS: electron impact mass spectroscopy

ESI-MS: electrospray mass spectroscopy

MALDI-MS: matrix assisted laser desorption/ionisation mass spectroscopy

The examples below relate to pharmaceutical compositions:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

EXAMPLE I

Inhalation Spray 14 g of active ingredient of the formula I are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

The invention claimed is:

1. A compound of formula I

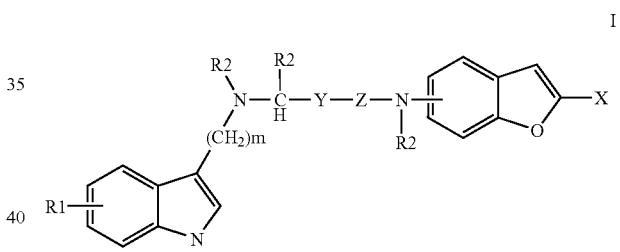

in which
R$^1$ denotes mono- or disubstitution by OH, OA, CN, Hal, COR or CH$_2$R,
Hal is F, Cl, Br, or I,
R is OH OA, NH$_2$, NHA or NA$_2$,
R$^2$ is, in each case independently, H, A, Ar, CH$_2$—Ar or CH$_2$—OH,
A is alkyl having 1, 2, 3, 4, 5 or 6 atoms,
Z is CH$_2$ or CO,
Y is a bond or CH$_2$,
X is CH$_2$OH, CH$_2$OA or COR, and
m is 2, 3, 4, 5 or 6,
or a pharmaceutically acceptable solvate, stereoisomer or salt thereof.

2. A compound according to claim 1, in which
R$^1$ is CN or F, and
R is NH2, O-methyl or O-ethyl,
or a pharmaceutically acceptable solvate, stereoisomer or salt thereof.

3. A compound according to claim 1, in which
R$^2$ is H or methyl, and
A is methyl or ethyl,
or a pharmaceutically acceptable solvate, stereoisomer or salt thereof.

4. A compound according to claim 1, in which
Z is CH$_2$ or CO,
or a pharmaceutically acceptable solvate, stereoisomer or salt thereof.

5. A compound according to claim 1, in which
X is COOC$_2$H$_5$, CONH$_2$ or CH$_2$OH,
or a pharmaceutically acceptable solvate, stereoisomer or salt thereof.

6. A compound according to claim 1, in which
m is 2 or 4,
or a pharmaceutically acceptable solvate, stereoisomer or salt thereof.

7. A compound according to claim 1, which is
ethyl 5-{2-[4-(5-cyano-1H-indol-3-yl)butylamino]ethanoylamino}benzofuran-2-carboxylate;
ethyl 5-{2-[3-(5-cyano-1H-indol-3-yl)propylamino]ethanoylamino}benzofuran-2-carboxylate;
ethyl 5-{2-[4-(5-cyano-1H-indol-3-yl)butylamino]ethylamino}benzofuran-2-carboxylate;
ethyl 5-{2-[4-(5-cyano-1H-indol-3-yl)butylamino]propanoylamino}benzofuran-2-carboxylate;
ethyl (R)-5-{2-[4-(5-cyano-1H-indol-3-yl)butylamino]propanoylamino}-benzofuran-2-carboxylate;
ethyl 5-{3-[4-(5-cyano-1H-indol-3-yl)butylamino]propanoylamino}benzofuran-2-carboxylate;
ethyl 5-(2-{[4-(5-cyano-1H-indol-3-yl)butyl]methylamino}ethanoylamino)-benzofuran-2-carboxylate;
ethyl (S)-5-{2-[3-(5-cyano-1H-indol-3-yl)propylamino]propanoylamino}-benzofuran-2-carboxylate;
2-[4-(5-cyano-1H-indol-3-yl)butylamino]-N-(2-hydroxymethylbenzofuran-5-yl)acetamide;
3-[4-{2-(2-hydroxymethylbenzofuran-5-ylamino)ethyl]methylamino}butyl)-1H-indole-5-carbonitrile;
C-{[4-(5-cyano-1H-indol-3-yl)butyl]methylamino}-N-(2-hydroxymethylbenzofuran-5-yl)acetamide;
5-(2-{[4-(5-cyano-1H-indol-3-yl)butyl]methylaminol}ethanoylamino)benzofuran-2-carboxamide; or
3-[4-(5-cyano-1H-indol-3-yl)butylamino]-N-(2-hydroxymethylbenzofuran-5-yl)propionamide;
or a pharmaceutically acceptable solvate, stereoisomer or salt thereof.

8. A process for preparing a compound of formula I according to claim 1 or a pharmaceutically acceptable solvate, stereoisomer or salt thereof, comrpising
a) reacting a compound of formula II

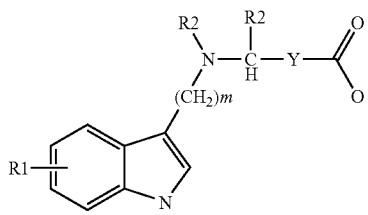

in which
R$^1$ denotes mono- or disubstitution by OH, GA, CN, Hal, COR or CH$_2$R,
Hal is F, Cl, Br, or I,
R is OH, GA, NH$_2$, NHA or NA$_2$,
R$^2$ is, in each case independently, H, A, Ar, CH$_2$—Ar or CH$_2$—OH,
A is alkyl having 1, 2, 3, 4, 5 or 6 atoms,
Y is a bond or CH$_2$, and
m is 2, 3, 4, 5 or 6,
with a compound of the formula III

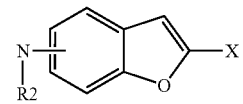

in which
R$^2$ is, in each independently, H, A. Ar, CH$_2$—Ar or CH$_2$—OH,
A is alkyl having 1, 2, 3, 4, 5 or 6 atoms,
X is CH$_2$OH, CH$_2$OA or COR, and
R is OH, GA, NH$_2$, NHA or NA$_2$,
or
b) reacting a compound of formula IV

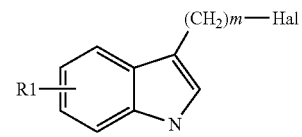

in which
R$^1$ denotes mono- or disubstitution by OH, OA, CN, Hal, COR or CH$_2$R,
Hal is F, Cl, Br, or I,
R is OH, OA, NH$_2$, NHA or NA$_2$,
A is alkyl having 1, 2, 3, 4, 5 or 6 atoms, and
m is 2, 3, 4, 5 or 6,
with a compound of the formula V

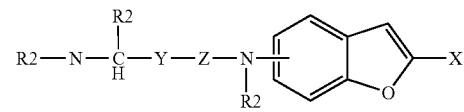

in which
R$^2$ is in each case independently, H, A, Ar, CH$_2$—Ar or CH$_2$—OH,
A is alkyl having 1, 2, 3, 4, 5 or 6 atoms,
Z is CH$_2$ or CO,
Y is a bond or CH$_2$,
X is CH$_2$OH, CH$_2$OA or COR, and
R is OH, OA, NH$_2$, NHA or NA$_2$,
and/or solvates by treatment with an acid or base or solvent.

9. A pharmaceutical composition comprising a compound according to claim 1 or a pharmaceutically acceptable solvate, stereoisomer or salt thereof, and a pharmaceutically acceptable excipient or adjuvant.

10. A pharmaceutical composition according to claim 9, furhter comprising a pharmaceutically active ingredient which is selected from the group consisting of levodopa, benserazide, carbidopa, bromocriptine, apomorphine, cabergoline, pramipexole, ropinirole, pergolide, dihydro-α-ergocriptine, lisuride, entacapone, tolcapone, selegiline, amantadine and budipine.

11. A pharamceutical set or kit comprising separate packs of
(a) a compound of the formula I according to claim 1 or a pharmaceutically acceptable solvate, stereoisomer or salt thereof, and
(b) a pharmaceutically active ingredient which is selected from the group consisting of levodopa, benserazide, carbidopa, bromocriptine, apomorphine, cabergoline, pramipexole, ropinirole, pergolide, dihydro-α-ergocriptine, lisuride, entacapone, tolcapone, selegiline, amantadine and budipine.

12. A compound according to claim 1, in which
$R^2$ is, in each case independently, H, A, or $CH_2$—OH,
or a pharmaceutically acceptable solvate, stereoisomer or salt thereof.

13. A compound of formula I

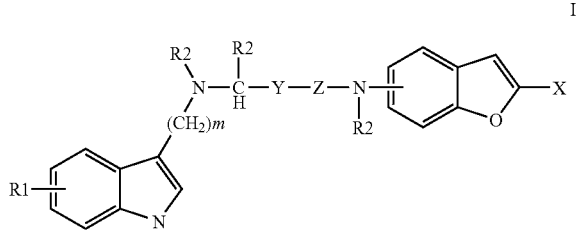

in which
$R^1$ denotes mono- or disubstitution by OH, GA, CN, Hal, COR or $CH_2R$,
Hal is F, Cl, Br, or I,
R is OH, OA, $NH_2$, NHA or $NA_2$,
$R^2$ is, in each case independently, H, A, Ar, $CH_2$—Ar or $CH_2$—OH,
A is alkyl having 1, 2, 3, 4, 5 or 6 atoms,
Z is $CH_2$ or CO,
Y is a bond or $CH_2$,
X is $CH_2OH$, $CH_2OA$ or COR, and
m is 2, 3, 4, 5 or 6,
or a pharmaceutically acceptable salt thereof.

14. A compound according to claim 13, in which
$R^2$ is, in each case independently, H, A, or $CH_2$—OH,
or a pharmaceutically acceptable salt thereof.

15. A compound according to claim 13, in which
Ar is an unsubstituted or mono- or polysubstituted benzene ring, an unsubstituted or substituted phenyl radical, or an unsubstituted or mono- or polysubstituted system of benzene rings, and anthracene, phenanthrene or naphthalene ring system, wherein the substituents are alkyl, alkoxy, oxo, hydroxyl, mercapto, amino, nitro, cyano or halogen radicals.

16. compound according to claim 13, in which
Ar is a benzene ring, or a phenyl radical, or an anthracene, phenanthrene or naphthalene ring system.

17. A compound according to claim 1, in which
Ar is an unsubstituted or mono- or polysubstituted benzene ring, an unsubstituted or substituted phenyl radical, or an unsubstituted or mono- or polysubstituted system of benzene rings, and anthracene, phenanthrene or naphthalene ring system, wherein the substituents are alkyl, alkoxy, oxo, hydroxyl, mercapto, amino, nitro, cyano or halogen radicals.

18. compound according to claim 1, in which
Ar is a benzene ring, or a phenyl radical, or an anthracene, phenanthrene or naphthalene ring system.

19. A compound according to claim 13, which is
ethyl 5-{2-[4-(5-cyano-1H-indol-3-yl)butylamino]ethanoylamino}benzofuran-2-carboxylate;
ethyl 5-{2-[3-(5-cyano-1H-indol-3-yl)propylamino]ethanoylamino}benzofuran-2-carboxylate;
ethyl 5-{2-[4-(5-cyano-1H-indol-3-yl)butylamino]ethylamino}benzofuran-2-carboxylate;
ethyl 5-{2-[4-(5-cyano-1H-indol-3-yl)butylamino]propanoylamino}benzofuran-2-carboxylate;
ethyl (R)-5-{2-[4-(5-cyano-1H-indol-3-yl)butylamino]propanoylamino}benzofuran-2-carboxylate;
ethyl 5-{3-[4-(5-cyano-1H-indol-3-yl)butylamino]propanoylamino}benzofuran-2-carboxylate;
ethyl 5-(2-{[4-(5-cyano-1H-indol-3-yl)butyl]methylamino}ethanoylamino)benzofuran-2-carboxylate;
ethyl (S)-5-{2-[3-(5-cyano-1H-indol-3-yl)propylamino]propanoylamino}benzofuran-2-carboxylate;
2-[4-(5-cyano-1H-indol-3-yl)butylamino]-N-(2-hydroxymethylbenzofuran-5-yl)acetamide;
3-(4-{[2-(2-hydroxymethylbenzofuran-5-ylamino)ethyl]methylamino}butyl)-1H-indole-5-carbonitrile;
C-{[4-(5-cyano-1H-indol-3-yl)butyl]methylamino}-N-(2-hydroxymethylbenzofuran-5-yl)acetamide;
5-(2-{[4-(5-cyano-1H-indol-3-yl)butyl]methylamino}ethanoylamino)benzofuran-2-carboxamide; or
3-[4-(5-cyano-1H-indol-3-yl)butylamino]-N-(2-hydroxymethylbenzofuran-5-yl)propionamide;
or a pharmaceutically acceptable salt thereof.

20. A compound according to claim 13, in which
$R^1$ is CN or F, and
R is $NH_2$, O-methyl or O-ethyl,
or a pharmaceutically acceptable salt thereof.

21. A compound according to claim 13, in which
$R^2$ is H or methyl, and
A is methyl or ethyl,
or a pharmaceutically acceptable salt thereof.

22. A compound according to claim 13, in which
Z is $CH_2$ or CO,
or a pharmaceutically acceptable salt thereof.

23. A compound according to claim 13, in which
X is $COOC_2H_5$, $CONH_2$ or $CH_2OH$,
or a pharmaceutically acceptable salt thereof.

24. A compound according to claim 13, in which
m is 2 or 4,
or a pharmaceutically acceptable salt thereof.

25. A pharmaceutical composition comprising a compound according to claim 13 or a pharmaceutically acceptable salt thereof, and a pharmaceutically acceptable excipient or adjuvant.

26. A solvate of a compound according to claim 1, said solvate being a mono- or dihydrate or addition compound with an alcohol.

27. A solvate of a compound according to claim 1, said solvate being a mono- or dihydrate or addition compound with methanol or ethanol.

* * * * *

UNITED STATES PATENT AND TRADEMARK OFFICE
CERTIFICATE OF CORRECTION

PATENT NO. : 7,262,216 B2
APPLICATION NO. : 10/545170
DATED : August 28, 2007
INVENTOR(S) : Gunter Holzemann It is certified that error appears in the above-identified patent and that said Letters Patent is hereby corrected as shown below:

Column 18, line 47, reads "OH OA," should read -- OH, OA, --
Column 18, line 60, reads "NH2," should read -- $NH_2$, --
Column 18, line 61, reads "stercoisomer" should read -- stereoisomer --
Column 19, line 2, reads "$CH_2$or" should read -- $CH_2$ or --
Column 19, line 3, reads "stercoisomer" should read -- stereoisomer --
Column 19, line 23, reads "propanoylamino}-benzofuran..." should read
-- propanoylamino}benzofuran... --
Column 19, line 27, reads "ethanoylamino)-benzofuran..." should read
-- ethanoylamino)benzofuran... --
Column 19, line 30, reads "propanoylamino}-benzofuran..." should read
-- propanoylamino}benzofuran... --
Column 19, line 36, reads "...5-evano..." should read -- ...5-cyano... --
Column 19, line 39, reads "methylaminol} ..." should read -- methylamino} ... --
Column 19, line 62, reads "OH, GA," should read -- OH, OA, --
Column 19, line 65, reads "OH, GA," should read -- OH, OA, --
Column 20, line 14, reads "H, A." should read -- H, A, --
Column 20, line 18, "OH, GA," should read -- OH, OA, --
Column 20, line 38, reads "of the formula V" should read -- of formula V --
Column 20, line 56, after "and/or" and before "solvates" insert -- converting a basic or acidic compound of formula I into one of its salts or --
Column 20, line 62, reads "furhter" should read -- further --
Column 21, line 1, reads "pharamceutical" should read -- pharmaceutical --
Column 21, line 3, reads "of the formula I" should read -- of formula I --
Column 21, line 30, reads "OH, GA," should read -- OH, OA, --

Signed and Sealed this

Eighth Day of April, 2008

JON W. DUDAS
*Director of the United States Patent and Trademark Office*